(12) United States Patent
Azam et al.

(10) Patent No.: US 9,687,831 B2
(45) Date of Patent: Jun. 27, 2017

(54) METHOD FOR GENERATING A PURIFIED CATALYST

(71) Applicant: SAUDI BASIC INDUSTRIES CORPORATION, Riyadh (SA)

(72) Inventors: Shahid Azam, Riyadh (SA); Roland Schmidt, Riyadh (SA); Mohammed Al-Hazmi, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/767,421

(22) PCT Filed: Mar. 10, 2014

(86) PCT No.: PCT/IB2014/059598
§ 371 (c)(1),
(2) Date: Aug. 12, 2015

(87) PCT Pub. No.: WO2014/141050
PCT Pub. Date: Sep. 18, 2014

(65) Prior Publication Data
US 2016/0016156 A1    Jan. 21, 2016

Related U.S. Application Data

(60) Provisional application No. 61/778,809, filed on Mar. 13, 2013.

(51) Int. Cl.
| | |
|---|---|
| *B01J 20/34* | (2006.01) |
| *B01J 31/02* | (2006.01) |
| *B01J 19/24* | (2006.01) |
| *C07F 7/00* | (2006.01) |
| *C07F 7/28* | (2006.01) |

(52) U.S. Cl.
CPC ............ *B01J 31/0212* (2013.01); *B01J 19/24* (2013.01); *B01J 31/0209* (2013.01); *C07F 7/003* (2013.01); *C07F 7/28* (2013.01); *B01J 2219/00076* (2013.01); *B01J 2219/00081* (2013.01); *B01J 2219/00083* (2013.01); *B01J 2219/24* (2013.01)

(58) Field of Classification Search
CPC ............ B01J 20/34; B01J 23/96; B01J 38/04
USPC ........................................................ 502/34
See application file for complete search history.

(56) References Cited

U.S. PATENT DOCUMENTS

| | | |
|---|---|---|
| 6,324,852 B1 | 12/2001 | Cheng |
| 2005/0137369 A1 | 6/2005 | Baugh et al. |
| 2005/0265905 A1 | 12/2005 | Young |
| 2008/0234433 A1 | 9/2008 | Asandei |
| 2013/0030120 A1 | 1/2013 | Lin et al. |

FOREIGN PATENT DOCUMENTS

| | | |
|---|---|---|
| CN | 2356741 Y | 1/2000 |
| CN | 1670039 a | 9/2005 |
| CN | 1670040 A | 9/2005 |
| CN | 201190107 Y | 2/2009 |
| CN | 101723377 A | 6/2010 |
| EP | 1078915 A1 | 2/2001 |
| GB | 2236694 A | 4/1991 |
| WO | 2004101629 A1 | 11/2004 |
| WO | 2007065184 A1 | 6/2007 |

OTHER PUBLICATIONS

Chinese Patent No. 101723377; Date of Publication: Jun. 9, 2010; Abstract Only, 2 pages.
Chinese Patent No. 1670039; Date of Publication: Sep. 21, 2005; Abstract Only, 2 pages.
Chinese Patent No. 1670040; Date of Publication: Sep. 21, 2005; Abstract Only, 2 pages.
Chinese Patent No. 201190107; Date of Publication: Feb. 4, 2009; Abstract Only, 2 pages.
Chinese Patent No. 2356741; Date of Publication: Jan. 5, 2000; Abstract Only, 1 page.
International Search Report for International Application No. PCT/IB2014/059598; Date of Mailing: Jul. 7, 2014; 5 pages.
Written Opinion of the International Searching Authority for International Application No. PCT/IB2014/059598; Date of Jul. 7, 2014; 7 pages.
Armarego, W.L.F., et al.;"Purification of Laboratory Chemicals", Butterworth-Heinemann, 2009, 6th edition, p. 31.
Wang, Zude, "Synthesis of N-Butyl Titanate"; Chemistry World, English Tranlsation, 13 pages.

*Primary Examiner* — Edward Johnson
(74) *Attorney, Agent, or Firm* — Cantor Colburn LLP

(57) ABSTRACT

Methods for generating a purified catalyst are provided. The method includes performing a reaction in a reaction vessel to generate a liquid catalyst and reaction products, purging the reaction products using an inert gas to form a purged catalyst, freezing the purged catalyst in the reaction vessel, and applying a vacuum to the reaction vessel while the purged catalyst thaws, wherein the vacuum removes residual reaction products to form a purified catalyst. Systems for generating a purified catalyst and a purified catalyst are also provided.

14 Claims, 2 Drawing Sheets

METHOD FOR GENERATING A PURIFIED CATALYST

This is the U.S. national stage of PCT Application No. PCT/IB2014/059598, filed on Mar. 10, 2014, the disclosure of which is incorporated herein by reference. Priority under 35 U.S.C. §119(a) and 35 U.S.C. §365(b) is claimed from U.S. Patent Application No. 61/778,809, filed Mar. 13, 2013, the disclosure of which is incorporated herein by reference.

FIELD

The presently disclosed subject matter relates to a process for generating catalysts. Particularly, the present application relates to a system and method for generating a purified catalyst or catalyst component.

BACKGROUND

Reactions performed for generating catalysts often result in the formation of unwanted reaction side products. Such products can be removed through various techniques, including, for example, purging techniques using an inert gas such as nitrogen. However, inert gas purging often results in further undesired levels of residual reaction products. These residual reaction products can include harmful gases trapped within the catalyst or catalyst component, which can cause variations in purity and performance of the catalyst. These residual reaction products can cause operational problems such as fouling or even deactivation (i.e., as catalyst poisons) of the catalyst.

There remains a need in the art for a system and method for generating a catalyst that not only reduces residual reaction products, but also minimizes variations in purity and performance of the catalyst. The presently disclosed subject matter provides such significant advantages over currently available systems and methods.

SUMMARY OF THE DISCLOSED SUBJECT MATTER

The presently disclosed subject matter is directed to a method for generating a purified catalyst or catalyst component. The method includes performing a reaction in a reaction vessel to generate a liquid catalyst and reaction products; purging the reaction products using an inert gas to form a purged catalyst; freezing the purged catalyst in the reaction vessel; and applying a vacuum to the reaction vessel while the purged catalyst thaws, wherein the vacuum removes residual reaction products to form a purified catalyst.

In non-limiting embodiments of the present application, freezing the purged catalyst includes supplying a coolant to rods within the reaction vessel. The coolant can be selected from the group consisting of dry ice, ice-water, water, liquid nitrogen, and combinations thereof. The vacuum can be applied proximate to the top of the reaction vessel. The vacuum can be applied until the purged catalyst is liquefied. Further, freezing the purged catalyst and applying the vacuum can each be repeated one or more times. The purified catalyst can include a catalyst component.

In certain embodiments of the present application, the reaction products include hydrogen chloride. For example, the following nonlimiting reactions exemplify hydrogen chloride as reaction products: $ZrCl_4 + 4C_3H_7COOH \rightarrow Zr(OOCC_3H_7)_4 + 4HCl$ or $TiCl_4 + 4C_4H_9OH \rightarrow Ti(OC_4H_9)_4 + 4HCl$.

In certain embodiments of the present application, the inert gas includes nitrogen. The method can further include bubbling a second inert gas through the purified catalyst. The inert gas and the second inert gas can be the same or different. The second inert gas can be nitrogen. The method can further include applying sonication to the reaction vessel.

In accordance with another embodiment of the present application, a system for generating a purified catalyst is provided. The system includes a reaction vessel configured to perform a reaction to generate a liquid catalyst and reaction products and a plurality of elongated rods in the reaction vessel. Each rod includes a purge line configured to provide an inert gas to purge the reaction products to form a purged catalyst and a coolant line configured to freeze the purged catalyst in the reaction vessel. The system also includes a vacuum line proximate to the top of the reaction vessel and configured to remove residual reaction products while the purged catalyst thaws to form a purified catalyst. In certain embodiments of the present application, the elongated rods are hollow, movable rods.

In accordance with another embodiment of the present application, a system for generating a purified catalyst is provided. The system includes a reaction vessel configured to perform a reaction to generate a liquid catalyst and reaction products and a coil in the reaction vessel. The coil includes a purge line configured to provide an inert gas to purge the reaction products to form a purged catalyst and a coolant line configured to freeze the purged catalyst in the reaction vessel. The system also includes a vacuum line proximate to the top of the reaction vessel and configured to remove residual reaction products while the purged catalyst thaws to form a purified catalyst. In certain embodiments of the present application, the coil is a hollow, movable coil.

Further, the systems for generating a purified catalyst can include any of the features described herein for the method of generating a purified catalyst.

In accordance with another embodiment of the present application, a purified catalyst is provided. The purified catalyst is prepared by the process including performing a reaction in a reaction vessel to generate a liquid catalyst and reaction products, purging the reaction products using an inert gas to form a purged catalyst, freezing the purged catalyst in the reaction vessel, and applying a vacuum to the reaction vessel while the purged catalyst thaws, wherein the vacuum removes residual reaction products to form a purified catalyst. The purified catalyst can comprise less than about 2000 ppm of the reaction products, less than 500 ppm, or less than 100 ppm. The purified catalyst can include any of the features described herein above for the method or system for generating a purified catalyst.

DETAILED DESCRIPTION

Figure 1:
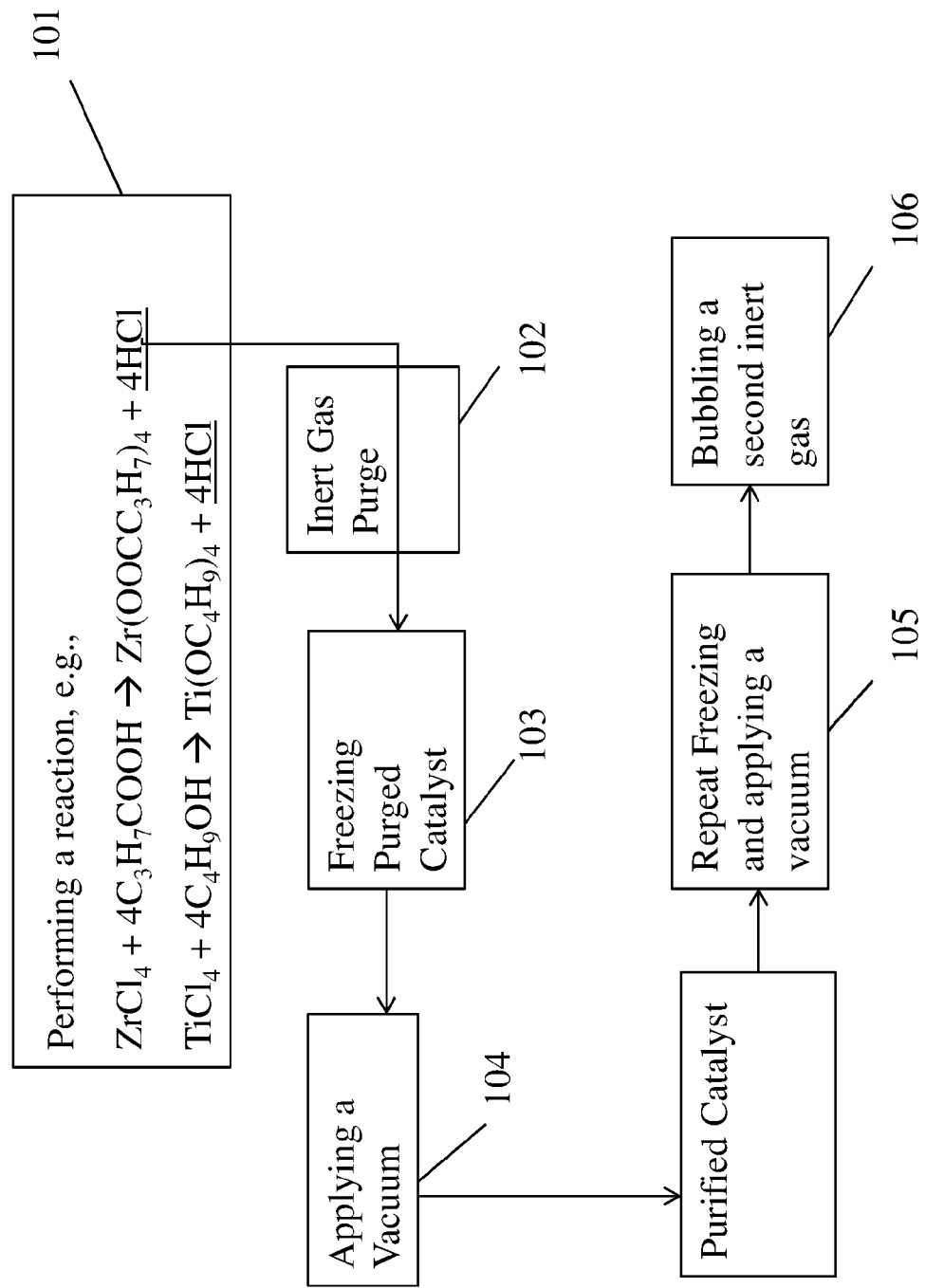
FIG. 1 is a flow diagram showing a method for generating a purified catalyst in accordance with one nonlimiting exemplary embodiment of the disclosed subject matter.

The foregoing has outlined rather broadly the features and technical advantages of the present application in order that the detailed description that follows can be better understood. Additional features and advantages of the application will be described hereinafter which form the subject of the claims of the application. It should be appreciated by those skilled in the art that the conception and specific embodiment disclosed can be readily utilized as a basis for modifying or designing other methods or systems for carrying out the same purposes of the present application. It should also be realized by those skilled in the art that such equivalent constructions do not depart from the spirit and scope of the application as set forth in the appended claims. The novel features which are believed to be characteristic of the application, together with further objects and advantages will be better understood from the following description.

The presently disclosed subject matter provides a system and method for generating a purified catalyst or catalyst component that reduces residual reactions products, which can cause variations in purity and performance of the catalyst, resulting from current systems and methods. For clarity and not by way of limitation, this detailed description is divided into the following sub-portions:

I. Definitions;
II. Method for Generating Purified Catalyst; and
III. System for Generating Purified Catalyst.

I. Definitions

The terms used in this specification generally have their ordinary meanings in the art, within the context of this application and in the specific context where each term is used. Certain terms are discussed below, or elsewhere in the specification, to provide additional guidance to the practitioner in describing the system and methods of the disclosed subject matter and how use and perform them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "substantially" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

The term "purified" as used herein refers to a catalyst or catalyst component that has been generated by a process that reduces or eliminates the presence of unrelated materials, i.e., reaction products, including unwanted or harmful reaction products and gaseous residual reaction products. Purified catalyst or catalyst components can be substantially free of reaction products and can be at least about 99% pure or at least 99.8% pure. Purity can be evaluated by any suitable methods known to one of ordinary skill in the art. For example, methods based on wet analysis such as titration using a potentiometer and a silver electrode can be used in the case, but not limited to, halogenides, e.g., HCl, are the undesired volatile component to be removed.

II. Method for Generating Purified Catalyst

For the purpose of illustration and not limitation, FIG. 1 is a flow diagram of a method for generating a purified catalyst in accordance with one embodiment of the disclosed subject matter. The method includes performing a reaction in a reaction vessel to generate a liquid catalyst and reaction products (101 as shown in FIG. 1). The reaction can be any reaction known to one of ordinary skill in the art for generating a desired catalyst or catalyst component. For example, the catalyst can be a zirconium catalyst and can be formed by $ZrCl_4 + 4C_3H_7COOH \rightarrow Zr(OOCC_3H_7)_4 + 4HCl$. Additionally or alternatively, the catalyst can be a titanium catalyst and can be formed by $TiCl_4 + 4C_4H_9OH \rightarrow Ti(OC4H_9)_4 + 4HCl$. The reaction products can include any products formed as a result of the desired catalyst reaction. In one embodiment, the reaction products can be harmful gases trapped within the catalyst or catalyst component, which can cause variations in purity and performance of the catalyst or catalyst component. For example, the reaction products can include hydrogen chloride.

Figure 2:
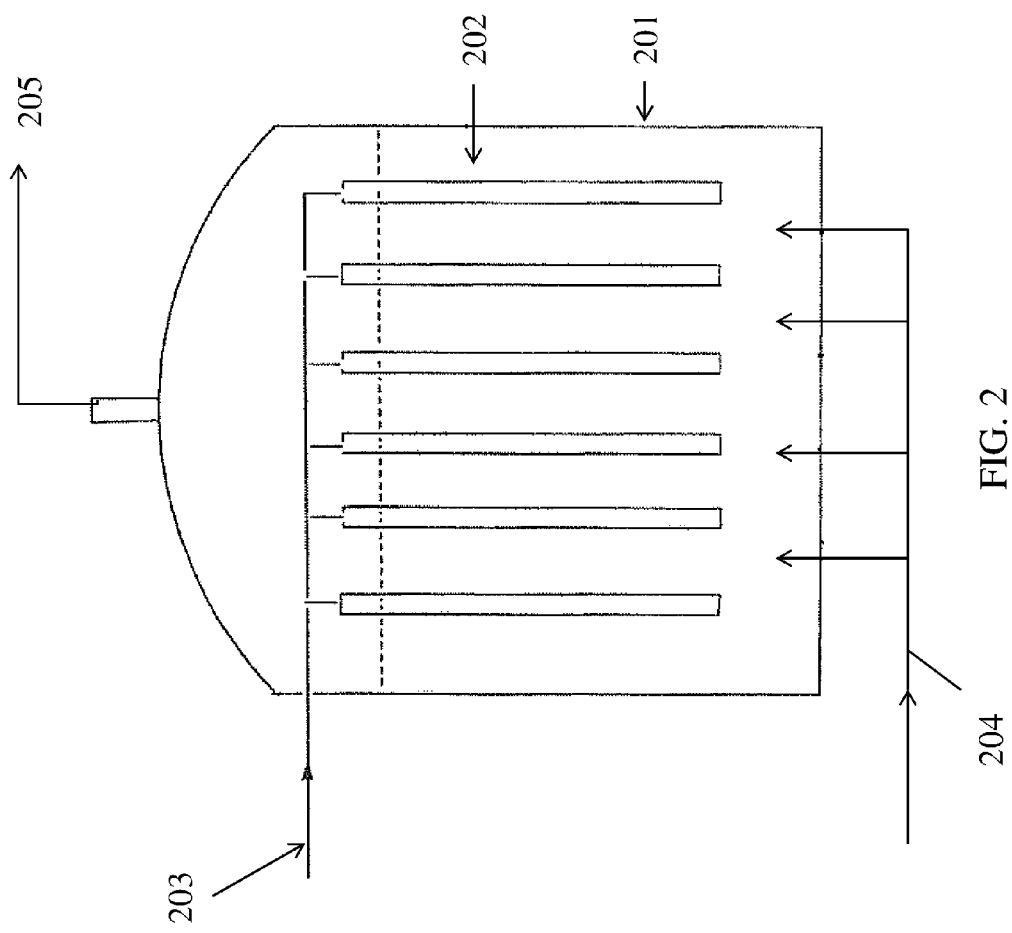
FIG. 2 shows a system for generating a purified catalyst in accordance with one nonlimiting exemplary embodiment of the disclosed subject matter.

The reaction vessel can be any suitable large-scale vessel known to one of ordinary skill in the art. For example, the reaction vessel is of a size and configuration that provides for even freezing and purging. For the purpose of illustration and not limitation, FIG. 2 shows a system for generating a purified catalyst including a reaction vessel 201.

The method also includes purging reaction products using a first inert gas to form a purged catalyst (102 as shown in FIG. 1). For example, the first inert gas can be bubbled through the catalyst and reaction products to separate and remove gaseous reaction products from the catalyst. Any suitable inert gas can be used, such as nitrogen. The first inert gas can be introduced using any suitable means known to one of ordinary skill in the art. In one embodiment, the inert gas is introduced through purge lines 203 and openings in rods 202 in reaction vessel 201, as shown in FIG. 2 for the purpose of illustration and not limitation. Alternatively, the first inert gas can be introduced through purge lines 204 provided proximate to the bottom of the reaction vessel 201.

The method also includes freezing the purged catalyst in the reaction vessel (103 as shown in FIG. 1). The purged catalyst can be frozen using any suitable means. For example, a coolant can be provided to rods 202 within the reaction vessel 201. Alternatively, the coolant can be provided to a cooling jacket on the reaction vessel 201 or to coils in or surrounding the reaction vessel 201. In one embodiment, the coolant can be a cooled gas that is bubbled through the purged catalyst. The coolant can be any suitable coolant known to one of ordinary skill in the art. For example, the coolant can be selected from the group consisting of dry ice, ice water, water, liquid nitrogen, and combinations thereof. The purification can be carried out in the reaction vessel at a temperature where the to-be-purified compound solidifies.

The method also includes applying a vacuum to the reaction vessel while the purged catalyst thaws so that the vacuum removes residual reaction products to form a purified catalyst (104 as shown in FIG. 1). The vacuum can be applied using any suitable means known to one of ordinary skill in the art. In one embodiment, the vacuum is applied via line 205 proximate to the top of the reaction vessel 201. The vacuum can be applied until the purged catalyst is liquefied. Depending on the desired purity of the catalyst, the purified catalyst can be refrozen and applying the vacuum can be repeated to increase the purity of the purified catalyst (105 as shown in FIG. 1). The freezing and applying the vacuum steps can each be repeated until a desired purity level is achieved.

In certain embodiments of the present application, the method can further include bubbling a second inert gas through the purified catalyst (106 as shown in FIG. 1). The first inert gas (used for the purging described above) and the second inert gas can be the same or a different inert gas. For example, the second inert gas can be nitrogen. The second inert gas can be introduced using any suitable means known to one of ordinary skill in the art. In one embodiment, the second inert gas is introduced through the purge lines 203 and openings in rods 202 as shown in FIG. 2. Alternatively, the second inert gas can be introduced through purge lines 204 provided proximate to the bottom of the reaction vessel 201.

In certain embodiments of the present application, the method can further comprise applying sonication to the reaction vessel using any suitable means known to one of ordinary skill in the art. In some embodiments, sonication can be provided while purging and/or applying the vacuum.

In accordance with another embodiment of the present application, a purified catalyst is provided. The purified catalyst can be prepared by the process described herein, which can have any of the additional or optional features described above. In one embodiment, the purified catalyst is at least about 99.8% pure, or comprises less than about 2000 parts per million (ppm) of the reaction products. In some embodiments, the purified catalyst comprises less than about 500, 100, or even 20 ppm of the reaction products. The purified catalyst can be a catalyst component.

III. System for Generating Purified Catalyst

FIG. 2 shows a system for generating a purified catalyst in accordance with one exemplary embodiment of the present application. The system includes a reaction vessel 201, which can be any suitable configuration for performing a reaction to generate a liquid catalyst and reaction products. For example, the reaction vessel can be sufficient for the large-scale generation of a catalyst. The system also includes plurality of elongated rods 202 in the reaction vessel 201. Each rod 202 can include a purge line 203 configured to provide an inert gas to purge the reaction products to form a purged catalyst and can include a coolant line 203 configured to freeze the purged catalyst in the reaction vessel. In some embodiments, for example, if the coolant is a cooled gas that is bubbled through the purged catalyst, the purge line and the coolant line are the same line 203. Additionally or alternatively, the system can include a jacket or coils for providing the coolant. The system also includes a vacuum line 205 proximate to the top of the reaction vessel and configured to remove residual reaction products while the purged catalyst thaws to form a purified catalyst. In one embodiment, the elongated rods 202 are hollow, movable rods that increase the efficiency of the purging and vacuuming steps. Furthermore, the system for generating a purified catalyst can include any of the features described herein above for the method for generating a purified catalyst.

The method of generating a purified catalyst, system for generating a purified catalyst, and purified catalyst disclosed herein include at least the following embodiments:

Embodiment 1: A method for generating a purified catalyst, comprising: performing a reaction in a reaction vessel to generate a liquid catalyst and reaction products; purging the reaction products using an inert gas to form a purged catalyst; freezing the purged catalyst in the reaction vessel; and applying a vacuum to the reaction vessel while the purged catalyst thaws, wherein the vacuum removes residual reaction products to form a purified catalyst.

Embodiment 2: The method of embodiment 1, wherein freezing the purged catalyst comprises supplying a coolant to rods within the reaction vessel.

Embodiment 3: The method of embodiment 2, wherein the coolant is selected from the group consisting of dry ice, ice-water, water, liquid nitrogen, and combinations thereof.

Embodiment 4: The method of any of embodiments 1-3, wherein the vacuum is applied proximate to the top of the reaction vessel.

Embodiment 5: The method of any of embodiments 1-4, wherein the vacuum is applied until the purged catalyst is liquefied.

Embodiment 6: The method of any of embodiments 1-5, wherein freezing the purged catalyst and applying the vacuum are each repeated one or more times.

Embodiment 7: The method of any of embodiments 1-6, wherein the reaction products comprise hydrogen chloride.

Embodiment 8: The method of any of embodiments 1-7, wherein the reaction comprises $ZrCl_4 + 4C_3H_7COOH \rightarrow Zr(OOCC_3H_7)_4 + 4HCl$.

Embodiment 9: The method of any of embodiments 1-7, wherein the reaction comprises $TiCl_4 + 4C_4H_9OH \rightarrow Ti(OC_4H_9)_4 + 4HCl$.

Embodiment 10: The method of any of embodiments 1-9, wherein the purified catalyst comprises a catalyst component.

Embodiment 11: The method of any of embodiments 1-10, wherein the inert gas comprises nitrogen.

Embodiment 12: The method of any of embodiments 1-11, further comprising bubbling a second inert gas through the purified catalyst.

Embodiment 13: The method of embodiment 12, wherein the inert gas and the second inert gas are the same.

Embodiment 14: The method of embodiment 12, wherein the inert gas and the second inert gas are the different.

Embodiment 15: The method of any of embodiments 13-14, wherein the second inert gas comprises nitrogen.

Embodiment 16: The method of any of embodiments 1-15, further comprising applying sonication to reaction vessel.

Embodiment 17: The method of any of embodiments 1-16, wherein the purified catalyst comprises less than about 2000 ppm of the reaction products.

Embodiment 18: A system for generating a purified catalyst, comprising: a reaction vessel configured to perform a reaction to generate a liquid catalyst and reaction products; a plurality of elongated rods in the reaction vessel, each rod comprising: a purge line configured to provide an inert gas to purge the reaction products to form a purged catalyst; and a coolant line configured to freeze the purged catalyst in the reaction vessel; and a vacuum line proximate to the top of the reaction vessel and configured to remove residual reaction products while the purged catalyst thaws to form a purified catalyst.

Embodiment 19: The system for generating a purified catalyst of embodiment 18, wherein the elongated rods are hollow, movable rods.

Embodiment 20: A system for generating a purified catalyst, comprising: a reaction vessel configured to perform a reaction to generate a liquid catalyst and reaction products; a coil in the reaction vessel, the coil comprising: a purge line configured to provide an inert gas to purge the reaction products to form a purged catalyst; and a coolant line configured to freeze the purged catalyst in the reaction vessel; and a vacuum line proximate to the top of the reaction vessel and configured to remove residual reaction products while the purged catalyst thaws to form a purified catalyst.

Embodiment 21: The system for generating a purified catalyst of embodiment 20, wherein the coil is a hollow, movable coil.

Embodiment 22: A purified catalyst prepared by the process comprising: performing a reaction in a reaction vessel to generate a liquid catalyst and reaction products; purging the reaction products using an inert gas to form a purged catalyst; freezing the purged catalyst in the reaction vessel; and applying a vacuum to the reaction vessel while the purged catalyst thaws, wherein the vacuum removes residual reaction products to form a purified catalyst.

Embodiment 23: The purified catalyst of embodiment 22, wherein the purified catalyst comprises less than about 2000 ppm of the reaction products.

Although the presently disclosed subject matter and its advantages have been described in detail, it should be understood that various changes, substitutions and alterations can be made herein without departing from the spirit and scope of the present application as defined by the appended claims. Moreover, the scope of the present application is not intended to be limited to the particular embodiments of the process, machine, manufacture, and composition of matter, means, methods and steps described in the specification. As an example, while the disclosed subject matter has been described in connection with a catalyst or catalyst component, the disclosed subject matter could also be used with any type of compound that results from substitution reactions and evolve smaller molecules that could harm or poison the desired compound or could be used in inorganic chemistry. As one of ordinary skill in the art will readily appreciate from the disclosure of the present application, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A method for generating a purified catalyst, comprising:
performing a reaction in a reaction vessel to generate a liquid catalyst and reaction products;
purging the reaction products using an inert gas to form a purged catalyst;
freezing the purged catalyst in the reaction vessel; and
applying a vacuum to the reaction vessel while the purged catalyst thaws, wherein the vacuum removes residual reaction products to form a purified catalyst.

2. The method of claim 1, wherein freezing the purged catalyst comprises supplying a coolant to rods within the reaction vessel.

3. The method of claim 2, wherein the coolant is dry ice, ice-water, water, liquid nitrogen, or a combination comprising at least one of the foregoing.

4. The method of claim 1, wherein the vacuum is applied proximate to the top of the reaction vessel.

5. The method of claim 1, wherein the vacuum is applied until the purged catalyst is liquefied.

6. The method of claim 1, wherein the reaction products comprise hydrogen chloride.

7. The method of claim 1, wherein the reaction comprises $ZrCl_4 + 4C_3H_7COOH \rightarrow Zr(OOCC_3H_7)_4 + 4HCl$.

8. The method of claim 1, wherein the reaction comprises $TiCl_4 + 4C_4H_9OH \rightarrow Ti(OC4H_9)_4 + 4HCl$.

9. The method of claim 1, wherein the inert gas comprises nitrogen.

10. The method of claim 1, further comprising bubbling a second inert gas through the purified catalyst.

11. The method of claim 10, wherein the inert gas and the second inert gas are the same or wherein the inert gas and the second inert gas are different.

12. The method of claim 11, wherein the second inert gas comprises nitrogen.

13. The method of claim 1, further comprising applying sonication to reaction vessel.

14. The method of claim 1, wherein the purified catalyst comprises less than about 2000 ppm of the reaction products.

* * * * *